United States Patent
Stevenson et al.

(10) Patent No.: US 9,204,655 B2
(45) Date of Patent: Dec. 8, 2015

(54) ANTIMICROBIAL SURFACE TREATMENT

(75) Inventors: Randal D. Stevenson, Cottage Grove, WI (US); Thomas J. Fahey, Okemos, MI (US)

(73) Assignee: DeVere Company, Inc., Janesville, WI (US)

( * ) Notice: Subject to any disclaimer, the term of this patent is extended or adjusted under 35 U.S.C. 154(b) by 61 days.

(21) Appl. No.: 13/303,267

(22) Filed: Nov. 23, 2011

(65) Prior Publication Data

US 2013/0052342 A1 Feb. 28, 2013

Related U.S. Application Data

(60) Provisional application No. 61/529,708, filed on Aug. 31, 2011.

(51) Int. Cl.
| | |
|---|---|
| *B05D 7/24* | (2006.01) |
| *B05D 5/00* | (2006.01) |
| *C09D 5/14* | (2006.01) |
| *A01N 59/00* | (2006.01) |
| *C11D 3/39* | (2006.01) |
| *C11D 3/395* | (2006.01) |
| *C11D 3/48* | (2006.01) |
| *A01N 25/12* | (2006.01) |

(52) U.S. Cl.
CPC ............... *A01N 59/00* (2013.01); *A01N 25/12* (2013.01); *C11D 3/3907* (2013.01); *C11D 3/3955* (2013.01); *C11D 3/48* (2013.01); *A61L 2209/22* (2013.01)

(58) Field of Classification Search
CPC .... A61L 2209/22; C11D 3/48; C11D 3/3955; A01N 25/12; A01N 59/00; A01N 59/02; A01N 59/14; A01N 59/26; A01N 43/64; A01N 2300/00
See application file for complete search history.

(56) References Cited

U.S. PATENT DOCUMENTS

| | | | |
|---|---|---|---|
| 3,706,670 A | 12/1972 | Gray | |
| 4,466,897 A * | 8/1984 | Appel et al. | 510/353 |
| 6,534,075 B1 | 3/2003 | Hei et al. | |
| 6,846,798 B2 * | 1/2005 | Joye et al. | 510/506 |
| 2006/0030506 A1 * | 2/2006 | Song et al. | 510/382 |
| 2008/0014284 A1 | 1/2008 | Meyer et al. | |

FOREIGN PATENT DOCUMENTS

| | | | |
|---|---|---|---|
| JP | 60-112714 | * | 6/1985 |
| WO | WO 99/64553 A1 | | 12/1999 |
| WO | WO 00/57703 A1 | | 10/2000 |
| WO | WO 2010/124823 A1 | | 11/2010 |

OTHER PUBLICATIONS

Oota, M. et al. Production of foamable granular composition having storage stability, JP 60-112714, published: Jun. 19, 1985, English Abstract obtained from ProQuest Dialog on Aug. 10, 2014.*
Oota, M. et al. Granulated Foaming Composition Having Storage Stability and Method of Production Thereof, JP 60-112714, published: Jun. 19, 1985, English Machine Translatation obtained: Aug. 2014.*
International Search Report and Written Opinion for PCT/US12/53449 mailed Dec. 13, 2012.
Best et al., "Efficacy of a variety of disinfectants against *Listeria* spp.," *Appl. Environ. Microbiol.*, 56(2): 377-380 (1990).
Ceylan, Erdogan, "Validation of quaternary ammonia and hydrogen peroxide powder for control of *Listeria monocytogenes* in ready-to-eat meat and poultry plants," Jul. 14, 2011 (obtained from the AMI Foundation website http://www.amif.org/research/09-416/ on Jan. 18, 2012).
Chambers et al., "Bactericidal Efficiency of Q.A.C. in Different Waters", *Public Health Reports*, vol. 70, No. 6, 545-553 (Jun. 1955).
U.S. Fire Administration Technical Report USFA-TR-27, Appendix E (1988).
Material Safety Data Sheet (MSDS) Santa Cruz Biotechnology MSDS for Sodium Dichloroisocyanurate, sc-253580 accessed online at <<http://datasheets.scbt.com/sc-253580.pdf>> on Feb. 10, 2014.
Material Safety Data Sheet (MSDS) *Sigma-aldrich* Version 5.2, Revision Date Jan. 17, 2012, accessed online at <<http://www.sigmaaldrich.com/catalog/product/aldrich/218928?lang=en&region=US >> on Feb. 10, 2014.
Josowitz, Alex, "Dry Floor Products Won't Slip Up," *Food Quality & Safety*, Jun./Jul. 2013.
Hegstad et al., "Does the wide use of quaternary ammonium compounds enhance the selection and spread of antimicrobial resistance and thus threaten our health?," *Microb Drug Resist.*, 16(2): 91-104 (Jun. 2010) (abstract only).
University of Iowa *Environmental Health and Safety Biological Safety Manual*, Chapter 8.2.9: Quaternary Ammonium Compounds, accessed online at <<http://ehs.research.uiowa.edu/print/book/export/html/485>> on Feb. 10, 2014.
ChemOne Chemical Incompatibility List accessed online at <<www.chemone.com/default/other/chemical%20incompatibility%20list.pdf>> on Feb. 10, 2014.

* cited by examiner

*Primary Examiner* — Johann R Richter
*Assistant Examiner* — Genevieve S Alley
(74) *Attorney, Agent, or Firm* — Leydig, Voit & Mayer, Ltd.

(57) ABSTRACT

A surface treatment powder comprising (a) about 50 wt. % or more of a percarbonate, perphosphate, persulfate, peroxide or perborate salt; (b) about 0.2-10 wt. % of a chlorinated isocyanurate salt; and (c) a bleach activator, and method of using same to inhibit the growth of a microorganism on a surface.

23 Claims, 3 Drawing Sheets

ANTIMICROBIAL SURFACE TREATMENT

CROSS-REFERENCE TO RELATED APPLICATIONS

This patent application claims priority to U.S. Provisional Patent Application 61/529,708 filed on Aug. 31, 2011, which is incorporated by reference in its entirety.

BACKGROUND OF THE INVENTION

Maintaining sanitary conditions in food processing facilities is of critical importance. Contamination of food or food-producing animals can result in adverse health effects, financial losses, and damage to customer confidence. Pathogenic microorganisms such as *E. coli, Salmonella*, and *Listeria* can live on any surface that is not properly cleaned, particularly moist surfaces such as floors and drains. There remains a need for new compositions and methods that can effectively reduce or eliminate the population of pathogenic microorganisms on surfaces in food processing facilities that are susceptible to contamination.

BRIEF SUMMARY OF THE INVENTION

The invention provides a surface treatment powder comprising (a) about 50 wt. % or more of a percarbonate, perphosphate, persulfate, peroxide or perborate salt; (b) about 0.2-10 wt. % of a chlorinated isocyanurate salt; and (c) a bleach activator. The invention also provides a method of inhibiting the growth of a microorganism on a surface comprising applying the surface treatment powder the surface and combining the surface treatment powder with water.

BRIEF DESCRIPTION OF THE SEVERAL VIEWS OF THE DRAWING(S)

DETAILED DESCRIPTION OF THE INVENTION

Figure 1:
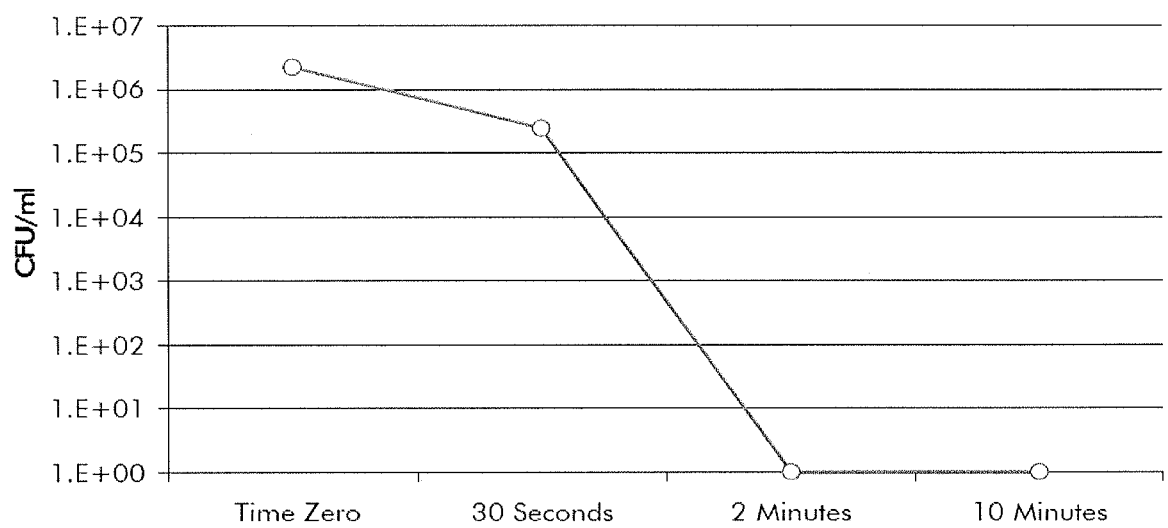
FIG. 1 is a graph of the concentration of viable *E. coli* colonies (colony forming units (CFU)/ml) plotted against time after application of a surface treatment powder.

Provided herein is a surface treatment powder comprising (a) about 50 wt. % or more of a percarbonate, perphosphate, persulfate, peroxide or perborate salt; (b) about 0.2-10 wt. % of a chlorinated isocyanurate salt; and (c) a bleach activator. Without wishing to be bound by any particular theory or mechanism of action, it is believed that the combination of the percarbonate, perphosphate, persulfate, peroxide or perborate salt, chlorinated isocyanurate salt, and bleach activator in the amounts provided, perhaps in further combination with other components described herein, act in synergy to provide a particularly effective antimicrobial surface treatment when applied to a wet surface or otherwise combined with water.

Any percarbonate, perphosphate, persulfate, peroxide or perborate salt can be used. Examples of suitable percarbonate, perphosphate, persulfate, peroxide or perborate salts include alkali metal or alkaline earth metal salts, such as sodium, potassium, magnesium, lithium, or calcium percarbonate, perphosphate, persulfate, peroxide or perborate salts. Mixtures thereof also can be used. Furthermore, any amount of the percarbonate, perphosphate, persulfate, peroxide or perborate salt can be used, provided that the percarbonate, perphosphate, persulfate, peroxide or perborate salt constitutes about 50 wt. % or more of the powder composition. For instance, the composition can comprise about 60 wt. % or more, about 65 wt. % or more, about 70 wt. % or more, about 75 wt. % or more, about 80 wt. % or more, or even about 85 wt. % or more of the percarbonate, perphosphate, persulfate, peroxide or perborate salt.

Any chlorinated isocyanurate salt can be used in the surface treatment powder. Examples of chlorinated isocyanurate salts include alkali metal or alkaline earth metal salts, for instance, sodium dichloroisocyanurate, potassium dichloroisocyanurate, sodium trichloroisocyanurate, potassium trichloroisocyanurate, and mixtures thereof. The chlorinated isocyanurate is used in an amount equal to about 0.2-10 wt. % of the powder composition, such as about 0.2-5 wt. %, about 0.5-5 wt. %, or about 0.5-2 wt. %.

The bleach activator can be any compound that reacts with hydrogen peroxide to form a peracid. Thus, bleach activators are sometimes referred to as peracid precursors. Various bleach activators are known in the art. Examples of bleach activators include tetra acetyl ethylene diamine (TAED), Ethylenediamine (EDA), sodium nonanoyloxybenzenesulfonate (NOBS), Decanoic acid, 2-[[(4-sulfophenoxy) carbonyl]oxy] ethyl ester, sodium salt (DECOBS), and mixtures thereof. In one embodiment, the bleach activator comprises, consists essentially of, or consists of tetra acetyl ethylene diamine (TAED). The bleach activator can be used in any effective amount. According to one embodiment, about 0.01-1 wt. % of a bleach activator is used, such as about 0.05-1 wt %, or about 0.05-0.5 wt. %.

The surface treatment powder can further comprise an alkaline pH adjuster to maintain an alkaline pH when the surface treatment powder is used. Any alkaline pH adjuster suitable for a powder composition, which can be activated when the powder is combined with water, can be used. Examples of suitable alkaline pH adjusters include carbonate and bicarbonate salts (e.g., sodium, potassium, calcium, or magnesium salts and the like). The pH adjuster is used in an amount sufficient to establish a pH of about 8 or more (e.g., about 9 or more, about 10 or more, or about 12 or more) when the powder composition is combined with water. According to one embodiment, the surface treatment powder comprises about 5-15 wt. % of a carbonate salt, such as sodium carbonate.

The surface treatment powder can further comprise one or more surfactants, which helps to penetrate the surface to be treated, particularly where the surface is uneven, cracked, or porous, such as concrete surfaces. Any surfactant can be used, particularly low-foaming, non-ionic surfactants. Suitable surfactants include, for instance alcohol ethoxylates, alkyl phenol ethoxylates, fatty amine oxides, alkanolamides, EO/PO block copolymers, and alkyl amine ethoxylates. According to some embodiments, only a limited amount of surfactant is used, such as about 5 wt. % or less (e.g., about 0.1-5 wt. %), about 2 wt. % or less (e.g., about 0.1-2 wt. %), or even about 1 wt. % or less (e.g., about 0.1-1 wt. %).

The surface treatment powder is typically used in the form of a powder (i.e., a granular or particulate composition), but the surface treatment powder can be used in other forms as well. For instance, the surface treatment powder can be compacted, optionally with a binder, to form a compacted solid. Such a compacted solid can be made using routine techniques.

Other components commonly found in antimicrobial or sanitizing treatment powder compositions also can be used. For instance, the surface treatment powder can comprise additional oxidants, bleaches, or sanitizing agents such as quaternary ammonium compounds or iodophors. Other components might also include viscosity modifying agents, such as synthetic or natural polymers or gums; chemical heaters and catalysts, such as zeolites, calcium sulfate, calcium oxide, calcium peroxide, magnesium sulfate, magnesium chloride, magnesium bromide, phosphorous pentoxide, sodium acetate, ferric chloride, ferric bromide, aluminum chloride, and aluminum bromide, aluminum iodide, aluminum sulfate, aluminum iodide, calcium bromide, calcium chloride, ferrous iodide, ferrous sulfate, magnesium iodide, pyrophosphoric acid, zinc chloride, zinc sulfate, and mixtures thereof; binders, such as glutaric anhydride, maleic anhydride, alcohol ethoxylates, and homopolymers and/or copolymers of ethylene oxide and/or propylene oxide; enzymes; and proteins.

Although the surface treatment powder described herein can comprise these above-described other components, one advantage of the invention is that such other components are not needed to provide an effective surface treatment powder. For some applications, it may be advantageous to provide a composition that is substantially free (e.g., no effective amount, or about 1 wt. % or less, about 0.1 wt. % or less, or even about 0.01 wt. % or less or completely free) of one or more of the "other components" identified in the preceding paragraph. It is particularly advantageous that the surface treatment powder can be substantially free of additional antibacterial components such as quaternary ammonium compounds.

By way of further illustration, one embodiment of the surface treatment powder described herein comprises, consists essentially of, or consists of (a) about 50 wt. % or more (e.g., about 75 wt. % or more, or about 80% or more) of a percarbonate, perphosphate, persulfate, peroxide or perborate salt, such as sodium percarbonate; (b) about 0.2-10 wt. % (e.g., about 0.5-2 wt %) of a chlorinated isocyanurate salt, such as sodium or potassium dichloroisocyanurate; (c) about 0.01-1 wt. % (e.g., about 0.05-1 wt %, or about 0.05-0.5 wt. %) of a bleach activator, such as TAED, (d) about 5-15 wt. % of an alkaline pH adjuster, such as a carbonate salt (e.g., potassium or sodium carbonate); and (e) about 5 wt. % or less (e.g., about 2 wt. % or less or about 1 wt. % or less) wt. % of a surfactant, such as a non-ionic surfactant.

The surface treatment powder can be used for any purpose, but is believed to be particularly useful for inhibiting microbial growth on hard surfaces that are susceptible to contamination by pathogenic microorganisms. For example, the surface treatment powder provided herein might be used to treat hard surfaces such as floors, drains, counters or other surfaces in food processing facilities or diaries.

Thus, provided herein is a method of inhibiting the growth of a microorganism on a surface comprising (a) applying a surface treatment powder as described herein to the surface, and (b) combining the surface treatment powder with water, whereby the growth of a microorganism on the surface is inhibited.

Growth of a microorganism is inhibited, for the purposes of the invention, if the rate of growth, viability, or population of a microorganism is reduced by any degree with application of the method described herein as compared to the rate of growth, viability, or population of the microorganism in the absence of such treatment. Inhibition of the growth of a microorganism therefore includes retarding or preventing the growth of a microorganism on a surface that is relatively free of microorganisms (e.g., prophylactic use) as well as reducing the growth of a microorganism, or reducing or eliminating the population of a microorganism, on a surface that is contaminated with the microorganism. Inhibition of the growth of a microorganism can be determined by any suitable technique, such as by measuring the population of viable microorganisms (e.g., colony forming units) present on the surface before and after treating the surface as described herein, or by comparing the growth of a microorganism on a surface treated in accordance herewith to the growth of the same type of microorganism on a similar surface without treatment. Preferably, the growth of a microorganism is reduced by about 10-fold or more, about 20-fold or more, about 50-fold or more, about 100-fold or more, about 1000-fold or more, or even about 10,000-fold or more (e.g., about 100,000-fold or more) by the method of the invention. Fold reduction, as used herein, can also be expressed in terms of $Log_{10}$ reduction, wherein a 10-fold reduction is a 1-$Log_{10}$ reduction, a 100-fold reduction is a 2-$Log_{10}$ reduction, a 10,000-fold reduction is a 3-$Log_{10}$ reduction, etc. Desirably, such reduction is achieved within about 30 minutes of performing the method (e.g., applying the surface treatment powder to a surface and combining with water), preferably within about 20 minutes, within about 10 minutes, or even within about 5 minutes.

The surface treatment powder can be applied to a surface and combined with water, in accordance with the method described herein, by any suitable technique. For instance, the powder can be applied manually (e.g., sprinkling by hand), or by using a mechanical dispenser such as a broadcast spreader. The surface can be a wet surface, whereby the surface treatment powder is combined with water simply by applying the powder to the wet surface. Alternatively, or in addition, water can be applied to the surface after application of the powder.

As yet another alternative, the powder can be mixed with water as it is applied to the surface or immediately prior to applying the powder to the surface (e.g., at the point-of-use). For instance, the powder can be mixed with water in a container, and the resulting mixture or solution can be applied to a surface to be treated. Such a container might be a dispenser with a compartment in which the surface treated powder is combined with water and an outlet through which the resulting mixture or solution exits the container and flows onto the surface to be treated. Or, the powder can be added directly to a stream of water directed onto the surface to be treated.

If the powder is mixed with water prior to applying the composition to the surface to be treated, such application should be performed before the solution loses effectiveness. Thus, for instance, the method might comprise mixing the powder with water and applying the powder to a surface within about 5 minutes of mixing with water, such as within about 1 minute or even within about 30 seconds of combining with water.

Any amount of moisture will activate the surface treatment powder. Thus, only a small amount of water is needed, and the surface treatment powder applied to a wet surface will continue to treat the surface over a period of time. If the powder is premixed with water prior to application to a surface, the powder can be mixed with water in any ratio. For the purposes of illustration only, the powder can be mixed with water in a powder:water volume ratio of about 5:1 to about 20:1, such as about 7:1 to about 20:1, or even about 8:1 to about 12:1.

The surface to be treated can comprise any material, provided that it is not significantly reactive with the surface treatment powder after combining the powder with water, such that the treatment would negatively effect or destroy the surface. The surface generally will be a hard porous or non-porous surface such as concrete and other masonry surfaces, rubber, steel, stainless steel, wood, or plastic (polymeric) surface. The surface can be smooth or irregular, and can include any part of a food processing or dairy plant (e.g., floors walls, counters, drains, equipment, etc.).

The method of inhibiting the growth of a microorganism can further comprise cleaning the surface to be treated prior to application of the surface treatment powder. Cleaning the surface typically comprises applying a suitable detergent to the surface and rinsing the surface prior to application of the surface treating powder. Any suitable detergent can be used for this purpose. The method of inhibiting the growth of a microorganism also can comprise additional sanitizing steps prior to application of the surface treatment powder.

The methods described herein will find use for inhibiting the growth of many different types of microorganisms, especially pathogenic microorganisms. In food processing and dairy facilities, *E. coli, Salmonella* (e.g., *S. enterica*), and *Listeria* (e.g., *L. monocytogenes*) are particularly problematic microorganisms. It is believed that the method described herein is useful for inhibiting the growth of *E. coli, Salmonella* (e.g., *S. enterica*), and/or *Listeria* (e.g., *L. monocytogenes*).

The following example further illustrates the invention but, of course, should not be construed as in any way limiting its scope.

EXAMPLE 1

This example illustrates use of a surface treatment powder in accordance with the invention.

A surface treatment powder was prepared by combining the components identified in Table 1:

TABLE 1

| Material | Amount (wt. %) |
|---|---|
| Sodium Percarbonate | 88.5 |
| Sodium Carbonate | 10 |
| Sodium Dichloroisocyanurate | 1 |
| Non-ionic Surfactant (alcohol ethoxylate | 0.4 |
| Tetra Acetyl Ethylene Diamine | 0.1 |

Figure 2:
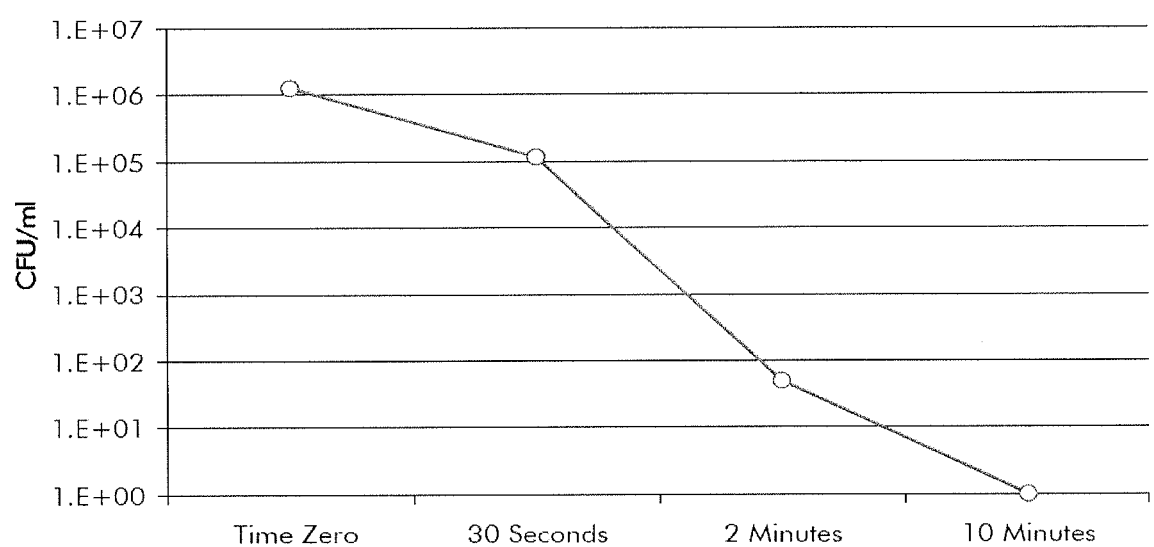
FIG. 2 is a graph of the concentration of viable *Listeria monocytogenes* colonies (CFU/ml) plotted against time after application of a surface treatment powder.
Figure 3:
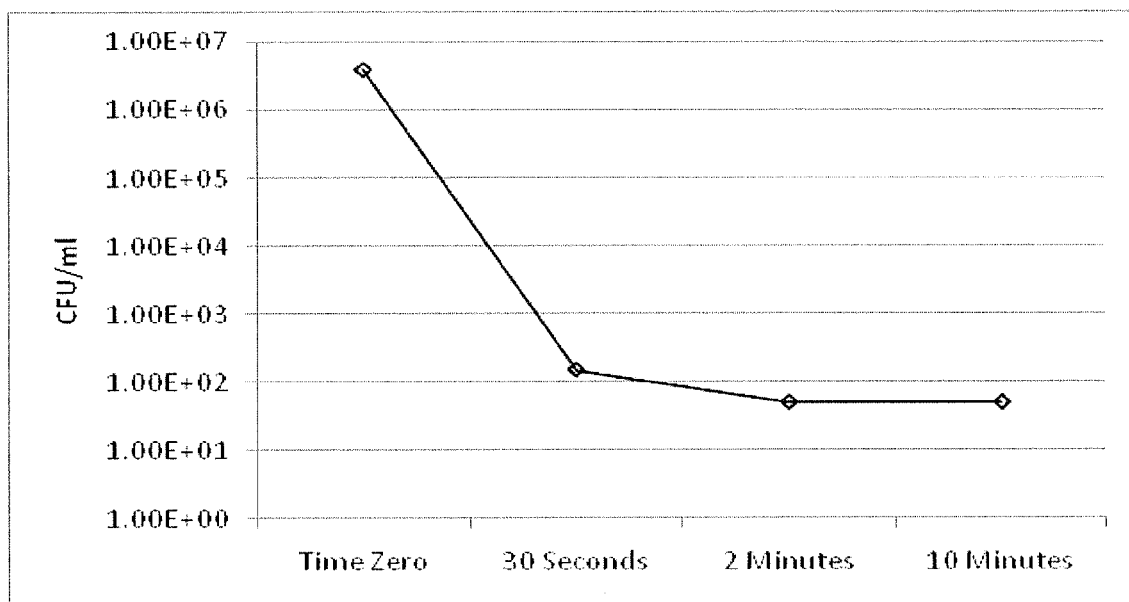
FIG. 3 is a graph of the concentration of viable *S. enterica* colonies (CFU/ml) plotted against time after application of a surface treatment powder.

To test the antimicrobial properties of the composition, the surface treatment powder was combined with water at a ratio of 1 g surface treatment powder to 29 ml of deionized water, and the resulting solution was used in a suspension time-kill study of *E. coli, L. monocytogenes,* and *S. enterica* bacteria. *E. coli* 11229, *L. monocytogenes* 15313, and *S. enterica* 10708 were separately grown in Tryptic Soy Broth for 24±6 hours, plated to Tryptic Soy Agar, and incubated at 36.0±1° C. for 24±6 hours. A small aliquot of each culture was placed in a reaction test vessel along with an aliquot of the surface treatment powder diluted with water. At each of time points 0, 30 seconds, 2 minutes, and 10 minutes, an aliquot was removed from the test vessel and placed into a neutralization broth. The samples collected at each time point were enumerated and plated to determine microbial concentration. The microbial concentrations at each time point were compared to the starting microbial concentration (time zero) to determine $Log_{10}$ reduction. The results are presented in FIG. 1 (*E. coli*), FIG. 2 (*L. monocytogenes*), and FIG. 3 (*S. enterica*), and corresponding Tables 2-4, below.

The results show that the surface treatment powder composition, when combined with water, provided a significant antimicrobial effect against *E. coli, L. monocytogenes,* and *S. enterica*, reducing the microorganisms to below detectible limits within 10 minutes.

TABLE 2

*E. coli*

| Contact Time (Minutes) | CFU/ml | Percent Reduction | Log Reduction |
|---|---|---|---|
| 0 | 2.25E+6 | N/A | N/A |
| 0.5 | 2.45E+05 | 89.111111% | 0.96 |
| 2 | <50 | >99.997778% | >4.65 |
| 10 | <50 | >99.997778% | >4.65 |

TABLE 3

*L. monocytogenes*

| Contact Time (Minutes) | CFU/ml | Percent Reduction | Log Reduction |
|---|---|---|---|
| 0 | 1.27E+06 | N/A | N/A |
| 0.5 | 1.16E+05 | 90.866142% | 1.04 |
| 2 | 5.00E+01 | 99.996063% | 4.40 |
| 10 | <50 | >99.996063% | >4.40 |

TABLE 4

*S. enterica*

| Contact Time (Minutes) | CFU/ml | Percent Reduction | Log Reduction |
|---|---|---|---|
| 0 | 3.95E+06 | N/A | N/A |
| 0.5 | 1.50E+02 | 99.996203% | 4.42 |
| 2 | <50 | >99.998734% | >4.90 |
| 10 | <50 | >99.998734% | >4.90 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A surface treatment powder comprising:
   (a) about 50 wt. % or more of a percarbonate, perphosphate, persulfate, peroxide or perborate salt;
   (b) about 0.2-10 wt. % of a chlorinated isocyanurate salt; and
   (c) a bleach activator,
   wherein the surface treatment powder is substantially free of binders.

2. The surface treatment powder of claim 1 further comprising an alkaline pH adjuster.

3. The surface treatment powder of claim 2, wherein the alkaline pH adjuster is a carbonate salt.

4. The surface treatment powder of claim 1 further comprising about 0.1-1 wt % of a surfactant.

5. The surface treatment powder of claim 1 comprising about 50 wt. % or more of a percarbonate salt.

6. The surface treatment powder of claim 1 comprising about 75 wt % or more of a percarbonate salt.

7. The surface treatment powder of claim 1 comprising about 0.2-10 wt % of a dichloroisocyanurate salt.

8. The surface treatment powder of claim 1 comprising about 0.5-2 wt. % of a dichloroisocyanurate salt.

9. The surface treatment powder of claim 1, wherein the bleach activator is tetra acetyl ethylene diamine (TAED).

10. The surface treatment powder of claim 9, comprising about 0.01-1 wt. % TAED.

11. The surface treatment powder of claim 9, comprising about 0.05-0.5 wt. % TAED.

12. The surface treatment powder of claim 1, wherein the surface treatment powder is substantially free of quaternary ammonium compounds.

13. The surface treatment powder of claim 1, wherein the surface treatment powder is substantially free of iodine or iodophors.

14. The surface treatment powder of claim 1, wherein the surface treatment powder is substantially free of enzymes.

15. A method of inhibiting the growth of a microorganism on a surface comprising applying the surface treatment powder of claim 1 to the surface and combining the surface treatment powder with water.

16. The method of claim 15, wherein the surface treatment powder is combined with water by applying the powder to a wet surface.

17. The method of claim 15, wherein the surface is concrete.

18. The method of claim 15, wherein the microorganism is *Listeria*, *S. enterica*, or *Escherichia coli*.

19. The surface treatment powder of claim 1, further comprising about 1 wt. % or less of a surfactant.

20. A surface treatment powder comprising:
   (a) about 50 wt. % or more of a percarbonate, perphosphate, persulfate, peroxide or perborate salt;
   (b) about 0.2-10 wt. % of a chlorinated isocyanurate salt; and
   (c) 0.05-0.5 wt. % of a bleach activator, wherein the surface treatment powder is substantially free of binders.

21. A surface treatment powder consisting essentially of:
   (a) about 50 wt. % or more of a percarbonate, perphosphate, persulfate, peroxide or perborate salt;
   (b) about 0.2-10 wt. % of a chlorinated isocyanurate salt;
   (c) about 0.05-0.5 wt. % of a bleach activator;
   (d) about 5-15 wt. % of an alkaline pH adjuster; and, optionally,
   (e) about 1 wt. % or less of a surfactant
   wherein the surface treatment powder does not comprise a compacted solid, and the surface treatment powder is substantially free of binders.

22. The surface treatment powder of claim 21, wherein the surface treatment powder comprises about 0.2-2 wt. % of a chlorinated isocyanurate salt.

23. The surface treatment powder of claim 22, wherein the surface treatment powder is substantially free of binders.

* * * * *